(12) United States Patent
Caron et al.

(10) Patent No.: US 8,697,894 B2
(45) Date of Patent: Apr. 15, 2014

(54) PREPARATION OF TAXANES FROM 9-DIHYDRO-13-ACETYLBACCATION III

(75) Inventors: Gaetan Caron, Quebec (CA); Mettilda Lourdusamy, Schererville (CA)

(73) Assignee: Accord Healthcare Ltd., Markham (CA)

( * ) Notice: Subject to any disclaimer, the term of this patent is extended or adjusted under 35 U.S.C. 154(b) by 689 days.

(21) Appl. No.: 13/031,378

(22) Filed: Feb. 21, 2011

(65) Prior Publication Data

US 2011/0144360 A1 Jun. 16, 2011

Related U.S. Application Data

(62) Division of application No. 11/909,973, filed as application No. PCT/CA2006/000480 on Mar. 30, 2006, now Pat. No. 8,263,793.

(60) Provisional application No. 60/666,728, filed on Mar. 31, 2005.

(51) Int. Cl.
C07D 305/00 (2006.01)
C07D 407/00 (2006.01)
C07D 493/00 (2006.01)

(52) U.S. Cl.
USPC ........................................ 549/510; 514/449

(58) Field of Classification Search
USPC ........................................ 549/510; 514/449
See application file for complete search history.

(56) References Cited

U.S. PATENT DOCUMENTS

| | | | |
|---|---|---|---|
| 5,476,954 | A | 12/1995 | Bourzat et al. |
| 5,637,732 | A | 6/1997 | Holton et al. |
| 5,705,508 | A | 1/1998 | Ojima et al. |
| 5,811,452 | A | 9/1998 | Ojima et al. |
| 5,889,043 | A | 3/1999 | Bouchard et al. |
| 6,043,375 | A | 3/2000 | Bourzat et al. |
| 6,090,951 | A | 7/2000 | Poss et al. |
| 6,175,023 | B1 | 1/2001 | Liu |
| 6,197,981 | B1 | 3/2001 | Liu |
| 6,281,368 | B1 | 8/2001 | McChesney et al. |
| 6,495,705 | B2 | 12/2002 | Chander et al. |
| 6,861,537 | B2 | 3/2005 | Holton et al. |
| 2001/0053857 | A1 | 12/2001 | Holton et al. |
| 2004/0225009 | A1 | 11/2004 | Kadow et al. |
| 2005/0272807 | A1* | 12/2005 | Naidu ............................ 514/449 |
| 2005/0288520 | A1 | 12/2005 | Naidu et al. |

FOREIGN PATENT DOCUMENTS

| | | |
|---|---|---|
| CA | 2 096 833 C | 6/1992 |
| CA | 2 119 261 C | 7/1994 |
| CA | 2165328 A1 | 12/1994 |
| CA | 2 214 319 C | 10/1996 |
| CA | 2188190 | 4/1998 |
| CA | 2204197 | 11/1998 |
| CA | 2 403 429 A1 | 9/2001 |
| CA | 2 444 693 A1 | 3/2004 |
| WO | WO 99/54322 A1 | 10/1999 |

OTHER PUBLICATIONS

Notification of Transmittal of the ISR and WO/International Search Report and Written Opinion of the International Search Authority, issued in corres. PCT/CA2006/000480, Jul. 14, 2006, ISA/CA—CIPO, Gatineau, Quebec, CA (Forms PCT/ISA/220; PCT/ISA/210; PCT/ISA/237).

Nikolakakis, Anastasia, et al., "*Taxus canadensis* Abundant Taxane: Conversion to Paclitaxel and Rearrangements," *Bioorcianic & Medicinal Chemistry*, 2000, pp. 1269-1280, vol. 8, Pergamon/Elsevier Science Ltd., UK.

Ojima, Iwao, et al., "Design, Synthesis and Structure—Activity Relationships of Novel Taxane-Based Multidrug Resistance Reversal Agents," *J. Med. Chem.*, 2005, pp. 2218-2228, vol. 48, No. 6, American Chemical Society, USA.

DeMattei, John. A., et al., "An Efficient Synthesis of the Taxane-Derived Anticancer Agent ABT-271," *J. Org. Chem.*, 2001, pp. 3330-3337, vol. 66, No. 10, American Chemical Society, USA.

* cited by examiner

*Primary Examiner* — Sarah Pihonak
(74) *Attorney, Agent, or Firm* — Buchanan Ingersoll & Rooney P.C.

(57) ABSTRACT

A new process for preparing a compound of Formula V, wherein P is a hydroxy protecting group and R is acetyl, said process including the steps of: i) selectively deacetylating the 10-hydroxy group of 9-dihydro-13-acetylbaccatin III with N,N-dimethylethylenediamine to produce 9-dihydro-10-deacetyl-13-acetyl-baccatin III; ii) concomitantly protecting 7-hydroxy and 10-hydroxy groups of the reaction product of step i); and iii) oxidizing the 9-hydroxy group of the reaction product of step ii) with an oxidizing agent to produce the compound of formula V.

3 Claims, No Drawings

PREPARATION OF TAXANES FROM 9-DIHYDRO-13-ACETYLBACCATION III

CROSS-REFERENCE TO RELATED APPLICATIONS

The present application is a divisional of U.S. application Ser. No. 11/909,973, filed on Sep. 27, 2007, which is a national stage application of Application No. PCT/CA2006/000480, filed on Mar. 30, 2006, which claims the benefit of U.S. provisional application No. 60/666,728 filed Mar. 31, 2005. The entire contents of each of U.S. application Ser. No. 11/909,973, Application No. PCT/CA2006/000480, and U.S. provisional application No. 60/666,728 are hereby incorporated herein by reference.

TECHNICAL FIELD

The present invention is directed towards a new method for the preparation of derivatives of 9-dihydrobaccatin III from 9-DHAB-III. It is also directed towards a new method to convert such derivatives of 9-dihydrobaccatin III into biologically active taxanes through coupling of suitable taxane side chains followed by oxidation of the 9 position. Such derivatives of 9-dihydrobaccatin III can be used as starting material for the synthesis of paclitaxel, docetaxel and analogs thereof.

BACKGROUND OF THE INVENTION

Paclitaxel, a naturally occurring diterpenoid extracted from yew trees, has demonstrated great potential as an anticancer drug. It is unique among antimitotic drugs in that it promotes the assembly of stable microtubules from tubulin. It binds strongly to microtubules, thus preventing depolymerisation of the tubulin and inhibiting mitosis. The structure of paclitaxel and the numbering system conventionally used is shown below. This numbering system is also applicable to compounds used in the process of the present invention.

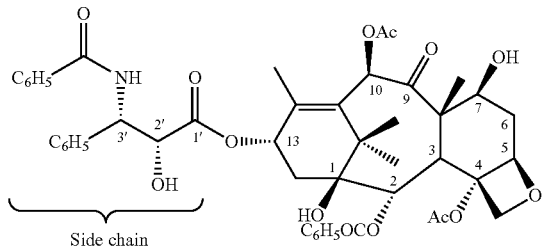

Side chain

The acyclic portion attached to the 13-hydroxy group is commonly referred to as "side chain" of a taxane compound.

Docetaxel, a paclitaxel derivative, has also demonstrated excellent antitumor activity over the past few years. Docetaxel has the following structure:

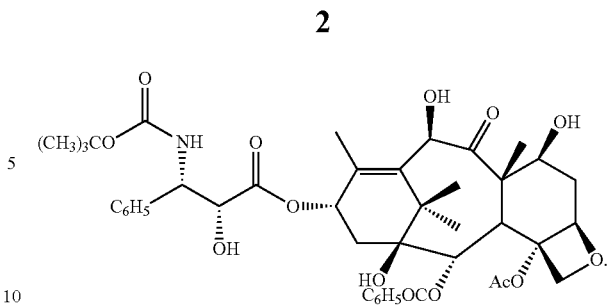

The chemical conversion of naturally occurring precursors such as 10-deacetylbaccatin III to paclitaxel and docetaxel have been reported. However, another potential precursor, 9-dihydro-13-acetylbaccatin III (9-DHAB-III), is abundant in needles and stems of the Canada yew, *Taxus canadensis*. The taxane structure of naturally occurring 9-DHAB-III has the carbon skeleton of paclitaxel and docetaxel except for the lack of a side chain and an alpha-hydroxyl group at C9. 9-DHAB-III has the following structure:

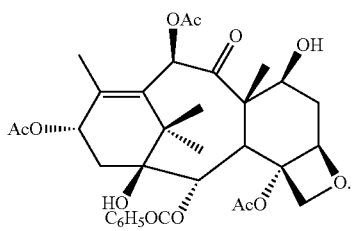

Synthetic routes that have been proposed for the synthesis of biologically active taxanes from 9-DHAB-III involve its conversion to baccatin III, 10-deacetylbaccatin III and 7-protected derivatives thereof. In this approach, a 7-protected-9-DHAB-III is oxidised at C9 followed by deacetylation at C10 and/or C13 (U.S. Pat. No. 6,197,981). Others have used 9-DHAB-III as starting material to produce novel 9-dihydro taxanes with potentially greater therapeutic benefits.

Important limitations and difficulties associated with existing methods using 9-DHAB-III as starting material include the difficult and low yield of deacetylation at 13-hydroxy group, poor scalability and the limited versatility of synthetic intermediates.

Earlier methods for the transformation of 9-DHAB III to 9-ketotaxanes bearing side chains involved the oxidation of the 9-hydroxy group prior to connecting the side chain to the baccatin A ring. A major difficulty with this approach is that the 13-acetoxy group of 7-protected-9-keto-baccatin III resists hydrolysis. Its removal requires strong bases such as alkyl lithium and the prior hydrolysis of the 10-acetoxy group resulting in overall low yield.

Another disadvantage is that the protection of the 7-hydroxy and 10-hydroxy groups in the synthesis of docetaxel and analogs thereof requires a separate step for protection of each position.

Therefore, additional routes for the production of biologically active taxanes are still needed.

It would thus be highly desirable to be provided with a new process for the preparation of paclitaxel, docetaxel, 9-dihydrobaccatin III, baccatin III and other taxanes from 9-DHAB-III.

SUMMARY OF THE INVENTION

One aim of the present invention is to provide a process for the preparation of paclitaxel, docetaxel, and analogs thereof where naturally occurring 9-DHAB-III or derivatives thereof are used as starting material.

Another aim of the present invention is to provide novel and versatile 9-dihydrobaccatin III derivatives as intermediates for the preparation of paclitaxel, docetaxel and other taxanes.

Another aim of the present invention is to provide a process for the preparation of 9-ketotaxane intermediates useful in the preparation of paclitaxel, docetaxel and analogs thereof using mild oxidation of the corresponding 9-dihydrotaxanes intermediates bearing protected side chains.

In one aspect of the invention, there is provided a process for the preparation of 9-dihydro-10-deacetylbaccatin III

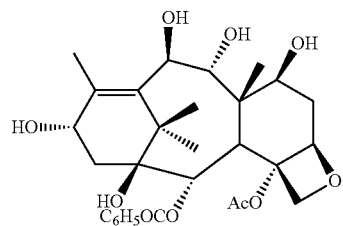

which comprises the step of reacting 9-dihydro-13-acetylbaccatin III having the formula:

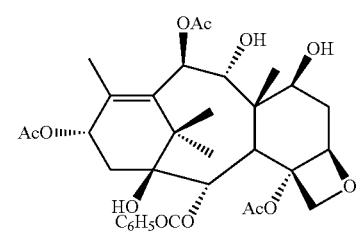

with a deacetylating agent in absence of a solvent to concomitantly deacetylate 10- and 13-positions and produce 9-dihydro-10-deacetylbaccatin III.

In accordance with the present invention, the process is further comprising the step of protecting the 7-hydroxy group of 9-dihydro-10-deacetylbaccatin III

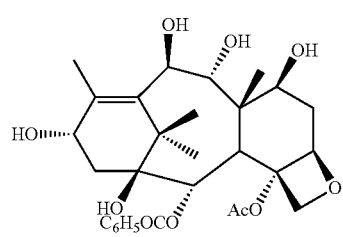

to produce a taxane of formula I

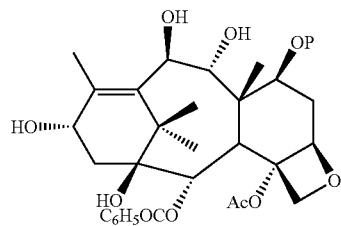

wherein P is a hydroxy protecting group.

In accordance with the present invention, the process is further comprising the step of acetylating the 10-hydroxy group of the taxane of formula I:

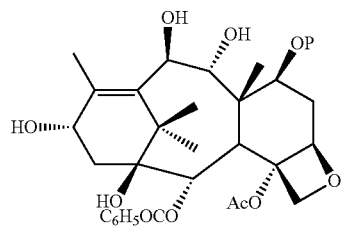

to produce a taxane of formula II:

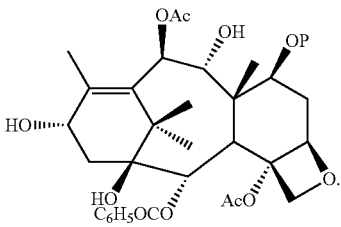

In accordance with the present invention, the process is further comprising the steps of:
i) reacting the 13-hydroxy group of the compound of formula II

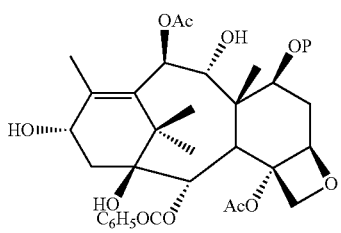

with a taxane side chain precursor of formula R—X, wherein X is a leaving group and R is

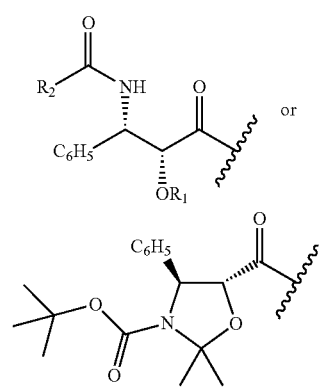

wherein $R_1$ is selected from the group consisting of ethoxyethyl, triethylsilyl, triisopropylsilyl, t-butyldimethylsilyl, t-butyldiphenylsilyl, benzyl and tert-butyloxycarbonyl and $R_2$ is phenyl or tert-butoxy; and ii) oxidizing the 9-hydroxy group with an oxidizing agent to produce a taxane of formula IV

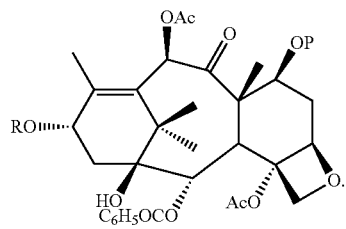

IV

In one aspect of the invention, there is provided a process for the preparation of 9-dihydro-10-deacetylbaccatin III as described herein; and further comprising the step of concomitantly protecting 10-hydroxy and 7-hydroxy groups of the 9-dihydro-10-deacetylbaccatin III

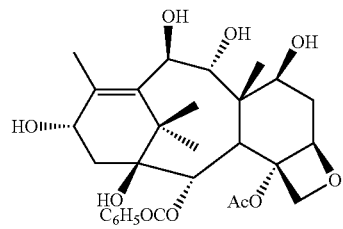

to produce a taxane of formula III

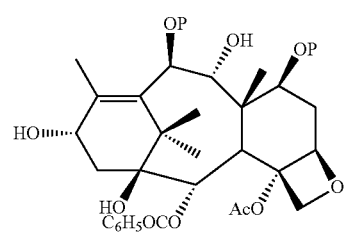

III wherein each P is the same and is a hydroxy protecting group.

In accordance with the present invention, the process is further comprising the steps of:

i) reacting the 13-hydroxy group of the compound of formula III

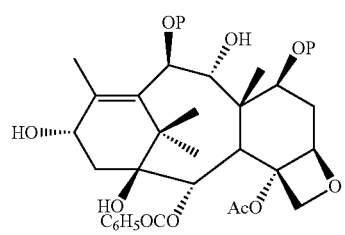

III with a taxane side chain precursor of formula R—X, wherein X is a leaving group and R is

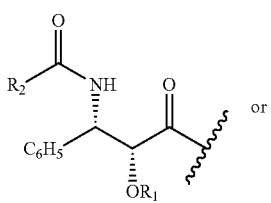

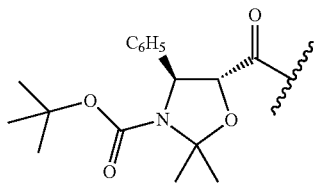

wherein $R_1$ is selected from the group consisting of ethoxyethyl, triethylsilyl, triisopropylsilyl, t-butyldimethylsilyl, t-butyldiphenylsilyl, benzyl and tert-butyloxycarbonyl and $R_2$ is phenyl or tert-butoxy; and ii) oxidizing the 9-hydroxy group with an oxidizing agent to produce a taxane of formula V

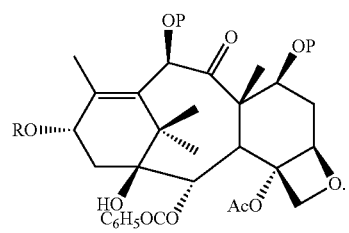

V

In accordance with the present invention, there is provided a process for the preparation of compound of formula V

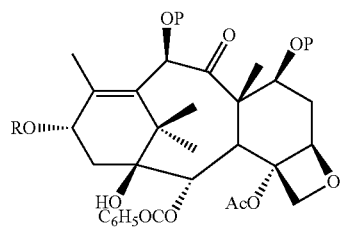

wherein P is a hydroxy protecting group and R is acetyl.

In accordance with the present invention, there is provided a process for producing a pharmaceutically active taxane which comprises the steps of i) producing a taxane of formula IV by the process as described herein; and ii) transforming said compound of formula IV into the pharmaceutically active taxane.

In accordance with the present invention, there is provided a process for producing a pharmaceutically active taxane, which comprises the steps of i) producing a taxane of formula V by the process as described herein; and ii) transforming said compound of formula V into the pharmaceutically active taxane.

DETAILED DESCRIPTION OF THE PREFERRED EMBODIMENT

In one embodiment, the present invention provides a new method for the preparation of 9-dihydro-10-deacetylbaccatin III from 9-DHAB III in one step and nearly quantitative yield. In the new method, no attempt is made to solubilize 9-DHAB III in preparation for deacetylation. Concentrated mixtures of 9-DHAB-III in hydrazine monohydrate or hydrazine hydrate in which 9-DHAB-III is insoluble or very sparingly soluble allow its complete conversion into 9-dihydro-10-deacetyl-baccatin III, which is also insoluble in these conditions.

The use of solvents such as ethanol used by other groups allows for the deacetylation of 10-hydroxy group only and requires an additional reaction step with strong nucleophiles such as methyllithium or n-butyllithium to deacetylate 13-hydroxy group.

In accordance with the present invention, there is also provided a process for the preparation of 9-dihydro-10-deacetylbaccatin III

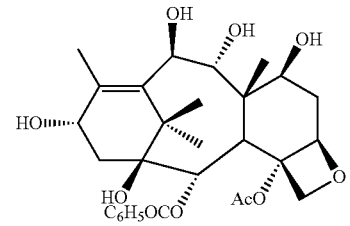

which comprises the step of reacting 9-dihydro-13-acetyl-baccatin III with a deacetylating agent, such as for example, hydrazine monohydrate, in absence of a solvent.

In one embodiment, the process is further comprising the step of washing the 9-dihydro-10-deacetylbaccatin III with an aqueous solvent.

In one embodiment, the aqueous solvent is water.

It is a further object of this invention to provide a simple and efficient method of preparing 7-protected-9-dihydro-10-deacetylbaccatin III of formula I

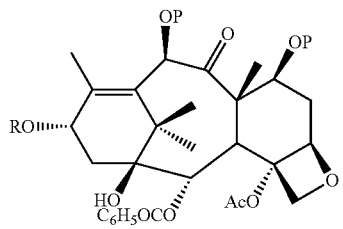

wherein P is a hydroxy protecting group and R is acetyl, said process comprising the steps of:

i) selectively deacetylating the 10-hydroxy group of 9-dihydro-13-acetylbaccatin III having the formula:

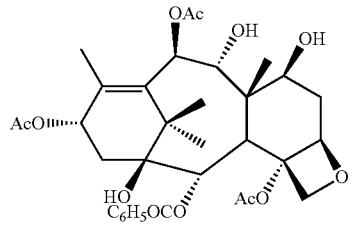

with N,N-dimethylethylenediamine to form 9-dihydro-10-deacetyl-13-acetyl-baccatin III of formula:

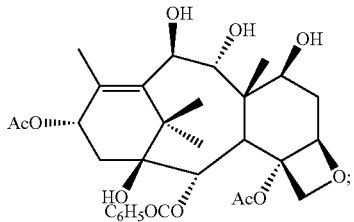

ii) concomitantly protecting 7-hydroxy and 10-hydroxy groups of the reaction product of step i); and iii) oxidizing the 9-hydroxy group of the reaction product of step ii) with an oxidizing agent to form the compound of formula V.

In accordance with the present invention, there is also provided a compound of formula I

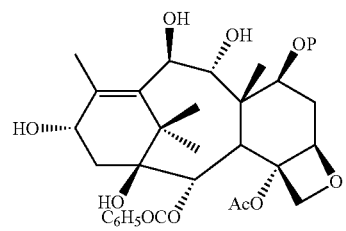

wherein P is a hydroxy protecting group.

In accordance with the present invention, there is also provided a compound of formula V

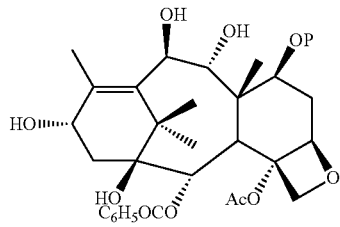

I

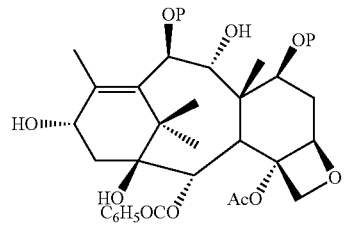

III wherein P is a hydroxy protecting group, which comprises the step of reacting 9-dihydro-10-deacetylbaccatin III with a hydroxy protecting group to form a compound of formula I.

In one embodiment, the 7-hydroxy group protection is highly regioselective.

The present invention also provides a process for the preparation of compound of formula II

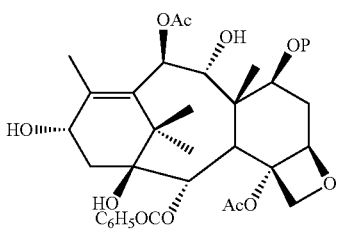

II which comprises the step of acylating a compound of formula I.

In one embodiment, the 10-hydroxy acetylation is highly regioselective.

In accordance with the present invention there is provided a process for the preparation of a taxane of formula II

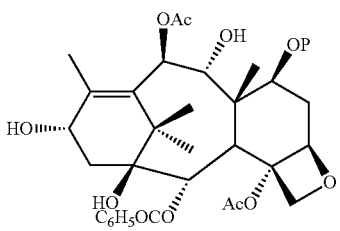

II wherein P is a hydroxy protecting group, said process comprising the steps of:
concomitantly deacetylating esters at the 10-position and 13-position of 9-dihydro-13-acetylbaccatin III to form 9-dihydro-10-deacetylbaccatin III;
protecting a hydroxy group at the 7-position of 9-dihydro-10-deacetylbaccatin III; and
acylating a hydroxy group at the 10-position to form a compound of formula II.

The present invention also provides a process for the selective and concomitant protection of 9-dihydro-10-deacetylbaccatin III at both C7 and C10 to afford a compound of formula III wherein P is a hydroxy protecting group, which comprises the step of reacting 9-dihydro-10-deacetylbaccatin III with a hydroxy protecting group to form a compound of formula III.

In one embodiment, the 7-, 10-bishydroxy group protection is highly regioselective.

In accordance with the present invention, there is also provided a process for the preparation of a taxane of formula III

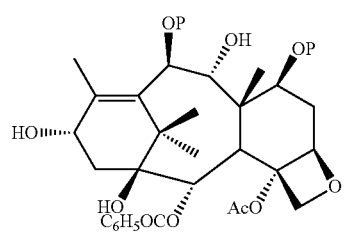

III wherein P is a hydroxy protecting group, said process comprising the steps of:
concomitantly deacetylating esters at the 10-position and 13-position of 9-dihydro-13-acetylbaccatin III to produce 9-dihydro-10-deacetylbaccatin III; and
concomitantly protecting hydroxy groups at the 7-position and 10 position of 9-dihydro-10-deacetylbaccatin III to form a compound of formula III.

The present invention further provides a process for the preparation of compound of formula IV

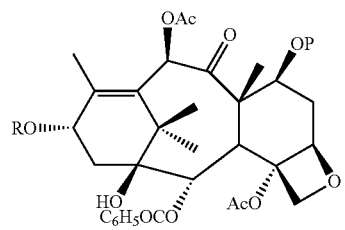

IV wherein P is a hydroxy protecting group and R is protected side chain, which comprises the step of: (i) reacting a compound of formula II at the 13 position with a suitable taxane side chain precursor; and (ii) oxidizing the hydroxyl group at the 9 position.

Compounds of formula IV can be converted to paclitaxel and analogs thereof.

The present invention further provides a process for the preparation of compound of formula V

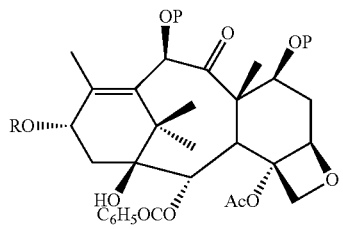

V wherein P is a hydroxy protecting group and R is protected side chain, which comprises the step of: (i) reacting a compound of formula III at the 13 position with a suitable taxane side chain precursor; (ii) oxidizing the hydroxyl group at the 9 position.

Compounds of formula V can be converted to docetaxel and analogs thereof.

Still in accordance with the present invention, there is also provided a process for the preparation of compound of formula V

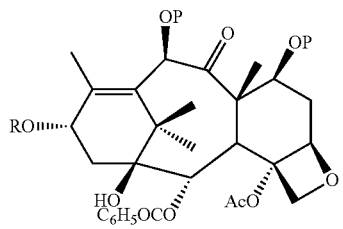

V wherein P is a hydroxy protecting group and R is acetyl, said process comprising the steps of:
  selectively deacetylating the ester at the 10-position of 9-dihydro-13-acetylbaccatin III with N,N-dimethylethylenediamine to form 9-dihydro-10-deacetyl-13-acetylbaccatin III;
  concomitantly protecting hydroxy groups at the 7-position and 10-position of 9-dihydro-10-deacetyl-13-acetylbaccatin III; and
  oxidizing the hydroxy group at the 9 position with an oxidizing agent to form a compound of formula V.

In accordance with the present invention, there is provided a process for producing a pharmaceutically active taxane which comprises the steps of i) producing a taxane of formula IV by the process as described herein; and ii) transforming said compound of formula IV into the pharmaceutically active taxane. In one embodiment, the pharmaceutically active taxane is paclitaxel.

In further embodiments, paclitaxel is paclitaxel anhydrous or trihydrates.

In accordance with the present invention, there is provided a process for producing a pharmaceutically active taxane, which comprises the steps of i) producing a taxane of formula V by the process as described herein; and ii) transforming said compound of formula V into the pharmaceutically active taxane. In one embodiment, the pharmaceutically active taxane is docetaxel.

In further embodiments, docetaxel is docetaxel anhydrous or trihydrates.

The present invention provides the advantage that starting material for the preparation of intermediates, 9-DHAB-III, is abundant in needles and twigs of the Canada yew, *Taxus Canadensis*.

For the purpose of the present invention the following terms are defined below.

The term "hydroxy protecting group" is intended to mean a group that is attached to the oxygen of the hydroxyl group, for protecting said group from reacting in a subsequent reaction. Such group are well known in the art.

In one embodiment, the protecting group is triethylsilyl, triisopropylsilyl, t-butyldimethylsilyl, t-butyldiphenylsilyl, benzyl or tert-butyloxycarbonyl, In one embodiment, the protecting group is triethylsilyl.

The term "protected taxane side chain" is intended to mean a side chain which when attached to the core molecules described herein will result in a taxane. The protected taxane side chain is said to be protected such that any reactive group on said side chain are prevented from reacting in any subsequent reaction until the protective group is removed. Such protective group is well known in the art. Moreover, the person skilled in the art will readily recognize the side chain required to produce a specific taxane when attached to the core molecules.

In one embodiment of the present invention, the taxane side chain precursor is of formula R—X, wherein R is

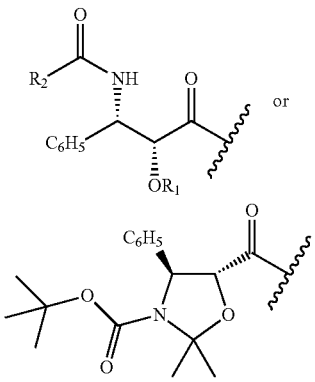

In one embodiment R is

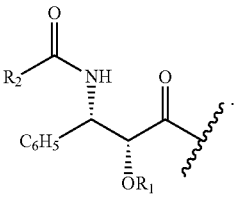

In one embodiment R is

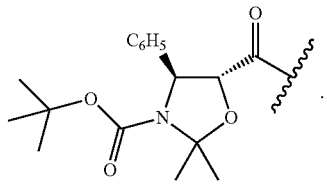

The term "deacetylating agent" means a reagent that has the ability to remove an acetyl group from the C-10 and C-13 hydroxyl of 9-dihydro-13-acetylbaccatin III. The deacetylating agent is a weak base being sufficiently nucleophilic to remove acetyl group. An appropriate agent should not have detrimental effect on other functionalities of the 9-dihydro-13-acetylbaccatin III and in particular C-2 benzoate or C-4 acetoxy groups. Non-limiting examples include hydrazine, methylhydrazine, 1,1-dimethylhydrazine, 1,2-dimethylhydrazine, 1,2-diethylhydrazine, phenylhydrazine or their hydrate thereof.

In one embodiment, the deacetylating agent is a nucleophilic weak base.

In one embodiment, the deacetylating agent is a hydrazine compound or its corresponding hydrate having the formula:

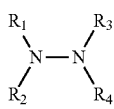

wherein each $R_1$ to $R_4$ is independently a hydrogen, an optionally substituted $C_1$-$C_6$ alkyl or an optionally substituted $C_6$ aryl.

In a further embodiment, each $R_1$ to $R_4$ is independently a hydrogen, a $C_1$-$C_4$ alkyl or a phenyl.

In a further embodiment, each $R_1$ to $R_4$ is independently a hydrogen, a methyl, an ethyl or a phenyl.

In one embodiment, the deacetylating agent is hydrazine, methylhydrazine, 1,1-dimethylhydrazine, 1,2-dimethylhydrazine, 1,2-diethylhydrazine, phenylhydrazine or their hydrate thereof.

In one embodiment, the deacetylating agent is hydrazine monohydrate.

As used herein, the term "solvent" means a liquid that partially or totally dissolves 9-dihydro-13-acetylbaccatin III.

The term "alkyl" represents a linear, branched or cyclic hydrocarbon moiety having 1 to 6 carbon atoms, which is optionally substituted. Examples include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, cyclopropyl, cyclobutyl, cyclopentyl and cyclohexyl. The term alkyl is also meant to include alkyls in which one or more hydrogen atom is replaced by a halogen, ie. an alkylhalide. Examples include but are not limited to trifluoromethyl, trichloromethyl, trifluoroethyl, trichloroethyl.

The term "aryl" represents a carbocyclic moiety containing one benzenoid-type ring and which may be optionally substituted with one or more substituents. Examples include but are not limited to phenyl, tolyl, dimethyphenyl, aminophenyl, anilinyl.

The term "independently" means that a substituent can be the same or a different definition for each item.

The terms "substituted" or "substituant" represent one or more halogen, amino, cyano, hydroxyl, nitro or acyl.

As used herein, the term "hydrate" in relation with "hydrazine" means that hydrazine incorporates water. Illustrative non-limiting examples include monohydrate, dihydrate, trihydrate and tetrahydrate or semi-hydrate. The hydration may be assessed by methods known in the art such as Loss on Drying techniques (LOD) and Karl Fisher titration.

The term "leaving group" herein refers to an atom or molecule that detaches from the group R— when exposed to an hydroxyl group of a taxane compound under usual reaction conditions. Examples include halogens such as chloride, bromide and iodide, sulfonates such as trifluoromethanesulfonate and methanesulfonate, azide, a derivative resulting from a carbodiimide such as N,N'-dicyclohexylcarbodiimide (DCC) N,N'-diisopropylcarbodiimide (DIC) or 1-ethyl-3-(3-dimethylaminopropyl) or carbodiimidehydrochloride (EDC).

"Oxidizing agent" that can be used in accordance with the present invention are for example, without limitation, o-iodoxybenzoic acid (IBX), 1,1,1-triacetoxy-1,1-dihydro-1,2-benziodoxol-3(1H)-one (Dess-Martin periodinane), iodosobenzene, iodozobenzene diacetate, $CrO_3/H_2SO_4$ (Jone's reagent), pyridinium dichromate, pyridinium chlorochromate, potassium permanganate and Swern reagent. Preferably, the oxidizing agent is 1,1,1-triacetoxy-1,1-dihydro-1,2-benziodoxol-3 (1H)-one.

The term "Swern reagent" herein refers to a reagent for oxidizing primary or secondary alcohols (hydroxyl groups) involving dimethylsulfoxide (DMSO) and anyone of a number of electrophilic molecule including but not limited to dicyclohexylcarbodiimide (DCC), acetic anhydride, trifluoroacetic anhydride, oxalyl chloride and sulphur trioxide.

In accordance with one embodiment of the present invention, it has been discovered that 9-DHAB-III can be deacetylated at both 10-hydroxy and 13-hydroxy groups under mild conditions and in near quantitative yields with hydrazine monohydrate. Surprisingly, it was discovered that neat hydrazine monohydrate (i.e. in the absence of a solvent) in which 9-DHAB-III is only sparingly soluble allows for complete deacetylation of the acetate at position C-13. Hydrazinolysis is highly selective and both 10- and 13-acetate are removed while the 4-acetoxy and 2-benzoate groups remain intact. That is in clear contrast with the techniques known in the art.

With reference to scheme 1. 1,9-DHAB-III (compound 3) was treated with neat hydrazine monohydrate, in accordance with the present invention, to yield the 9-dihydro-10-deacetylbaccatin III, (compound 4), that is also sparingly soluble in neat hydrazine monohydrate, and was then easily recovered by simple filtration. The 7-hydroxy group requires no protection during removal of the 10- and 13-acetate groups with base since the absence of a keto group at the 9-position prevents epimerisation of the 7-hydroxy group through a retro-aldol mechanism Compound 4 was converted to C-7-hydroxy-protected-10-acetoxy taxanes in two steps. First, the C-7 hydroxy group was protected with a hydroxy protecting group which in a preferred embodiment comprises silyl protecting groups in the presence of a catalyst such as 4-dimethylaminopyridine to yield compound 5. Second, the C-10 hydroxy group was acetylated selectively by reaction with acetyl chloride in pyridine to give compound 6.

Compound 4 was also converted into 7-,10-bis-protected taxanes 7 in a single step. In a preferred embodiment, trialkylsilylchloride was reacted with compound 4 in the presence 4-dimethylaminopyridine to yield compound 7.

Scheme 1

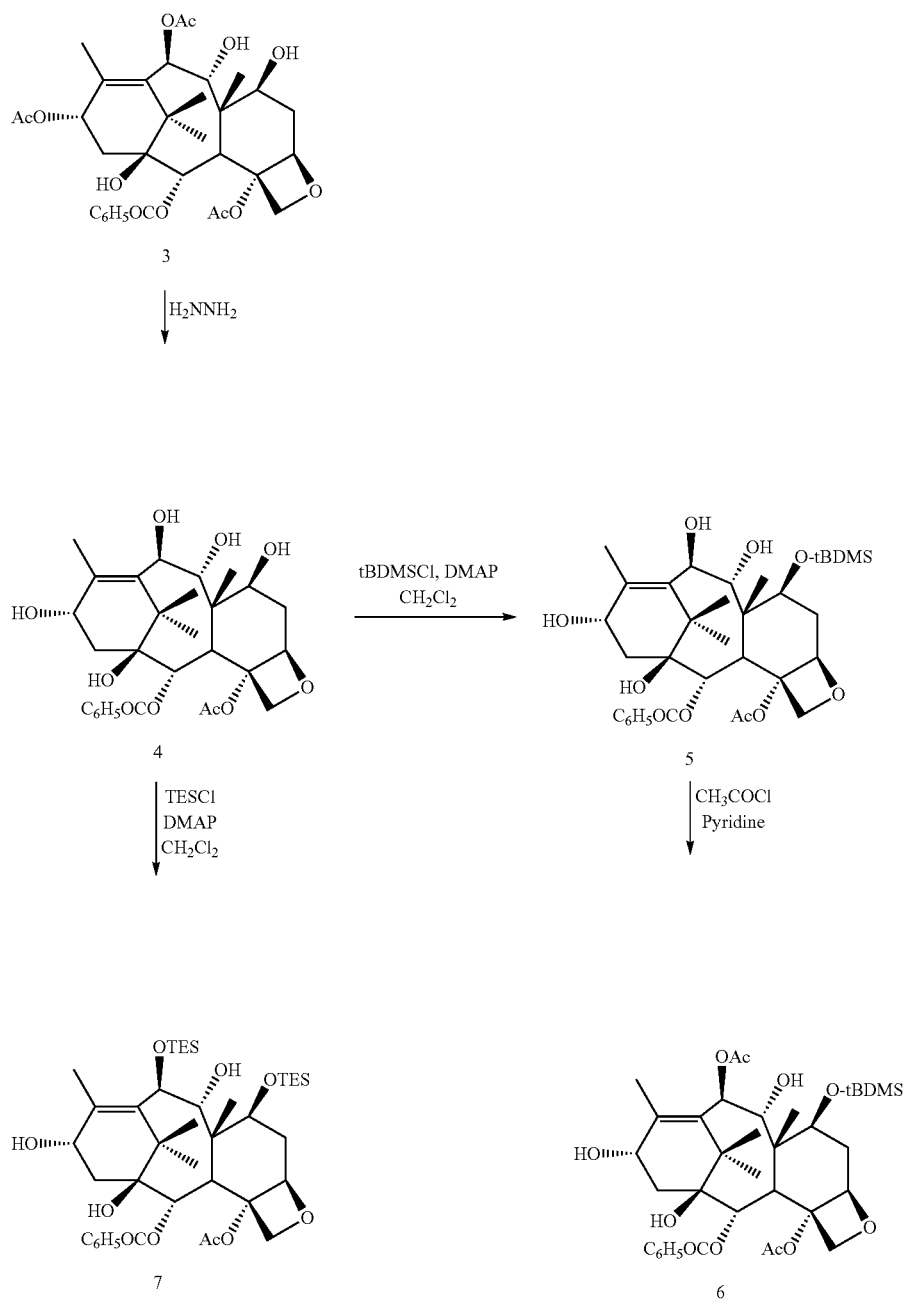

With reference to scheme 2,7-protected-10-acetyl taxanes such as compound 6 can be converted to biologically active taxanes such as paclitaxel bearing a side chain at the C-13-position, an acetyl group at the C-10-hydroxy group position and a carbonyl group at the C-9-position. This was accomplished in four steps: (1) coupling of compound 6 with a suitable side chain precursor; (2) oxidizing the 9-hydroxy group to a carbonyl group; (3) concomitant de-protection of the side chain and 7-position; and (4) acylation of the side chain amino group. In a preferred embodiment of the present invention, compound 6 was reacted with (4S,5R)-3-tert-butyloxyxcarbonyl-2,2-dimethyl-4-phenyl-5-oxazolidinecarboxylic acid in the presence of an activating agent which in a preferred embodiment comprises dicyclocarbodiimide and 4-dimethylaminopyridine to yield compound 8. Compound 8 was then converted to compound 9 shown in scheme 2 by reaction with the Dess-Martin periodinane. Compound 9 can then be converted to paclitaxel or other 10-acetyl taxanes in two steps using well-established chemistry for the de-protection of side chain and 7-position followed by the acylation of the amino group.

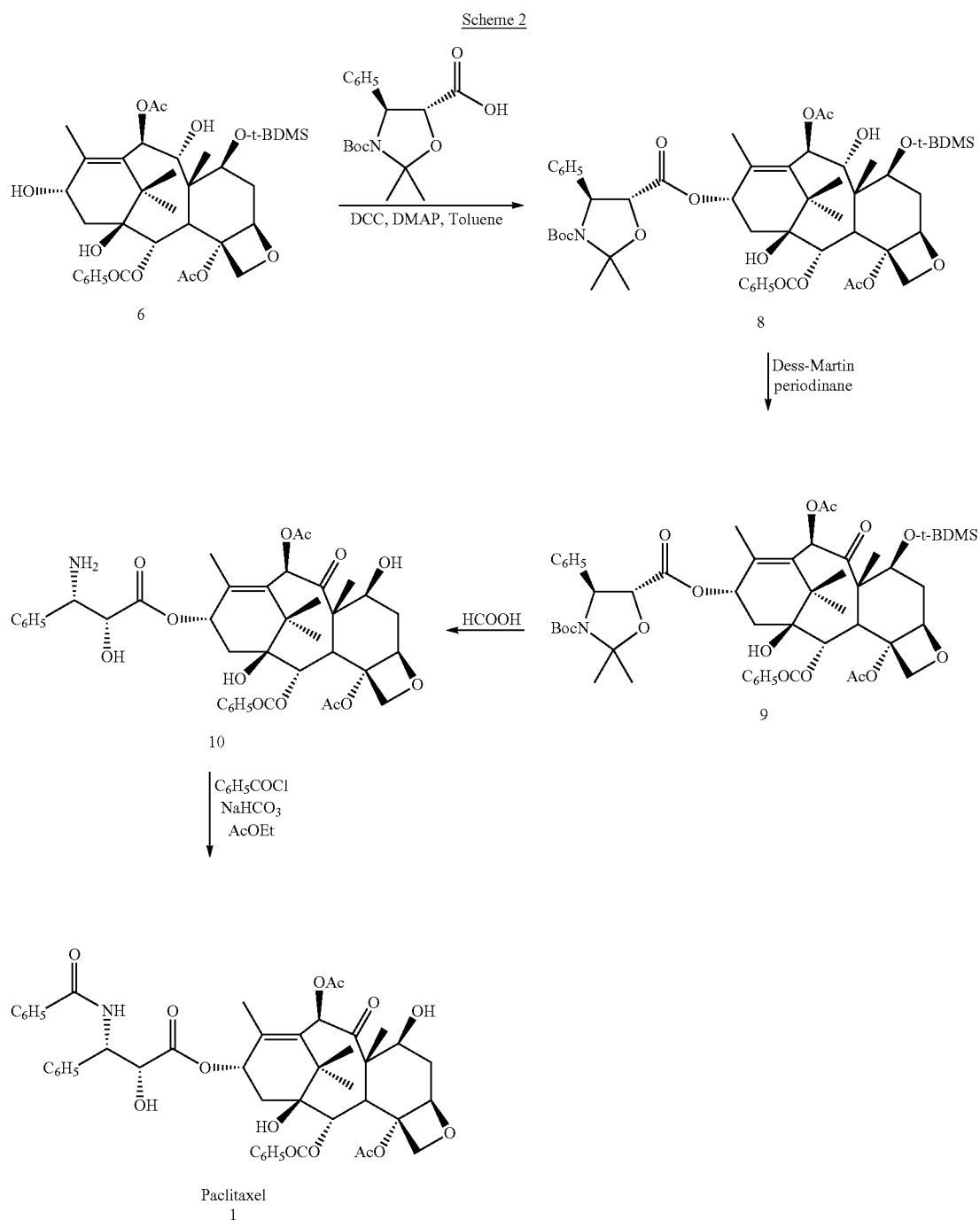

With reference to scheme 3, it is shown that 7,10-bis-protected-9-dihydro taxanes such as compound 7 can be converted to biologically active taxanes such as docetaxel bearing a side chain at the C-13-position, a carbonyl group at the C-9-position and free hydroxy groups at the C-7 and C-10 positions. This is accomplished in four steps: (1) coupling of compound 7 with a suitable side chain precursor; (2) oxidizing the 9-hydroxy group to a carbonyl group; (3) concomitant de-protection of the side chain and the C-7- and C-10-positions; and (4) acylation of the side chain amino group. In a preferred embodiment of the present invention, compound 7 was reacted with (4S,5R)-3-tert-butyloxyxcarbonyl-2,2-dimethyl-4-phenyl-5-oxazolidinecarboxylic acid in the presence of an activating agent which in a preferred embodiment comprises dicyclocarbodiimide and 4-dimethylaminopyridine to yield compound 11. Compound 11 was then converted to compound 12 shown in scheme 3 by reaction with the Dess-Martin periodinane. Compound 12 can then be converted to docetaxel or other 10-deacetyl taxanes in two steps using well-established chemistry for the de-protection of side chain and C-7- and C-10-position followed by the acylation of the amino group.

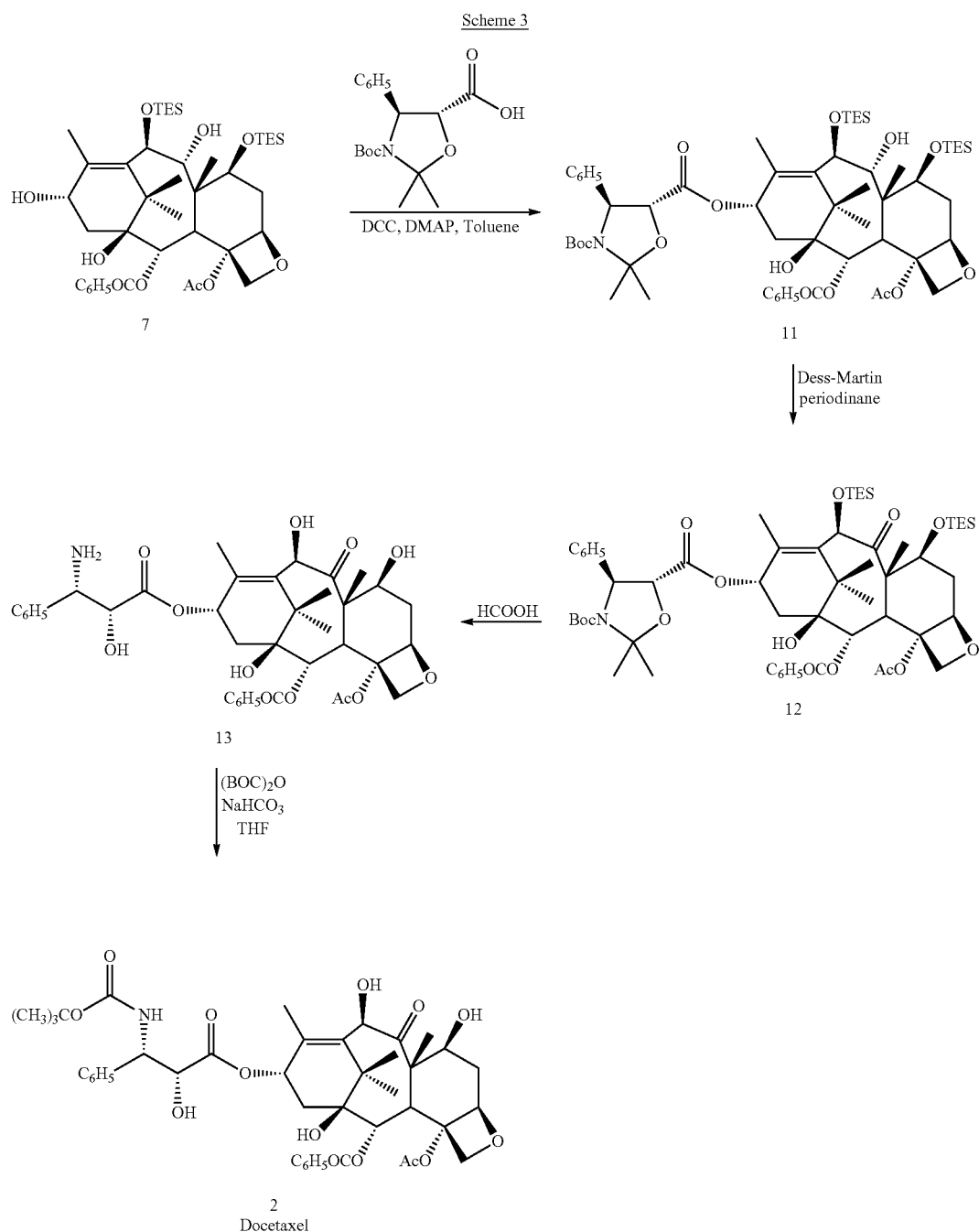

Scheme 3

With reference to scheme 4, this invention includes a process for the preparation of 7,10-bis-protected-13-acetyl-10-deacetylbaccatin III from 9-DHAB-III. Such compounds can be versatile precursors in the preparation of docetaxel and other taxanes. For example, they can be reacted with a side chain precursor at the C-13-position in the presence of an alkyl lithium according to known chemistry. The conversion from 9-DHAB-III is accomplished in three steps: (1) selective hydrolysis of the 10-acetyl group of 9-DHAB-III; (2) concomitant and selective protection at the C-7-, and C-10-positions; and (3) oxidation of the C-9-position.

It was discovered that N,N-dimethylethylenediamine is an excellent reagent for the removal of the 10-acetyl group of 9-DHAB-III. N,N-dimethylethylenediamine deacetylates 9-DHAB-III selectively and in nearly quantitative yields leaving the 13-acetoxy group intact. Furthermore, it requires no solvent and is removed easily from the reaction mixture by simple evaporation due to its relatively low boiling point. In a preferred embodiment of the present invention, the resulting product, compound 14 was reacted with triethylsilylchloride in the presence of 4-dimethylaminopyridine to yield compound 15. Compound 15 was then converted to compound 16 by reaction with Dess-Martin periodinane.

Scheme 4

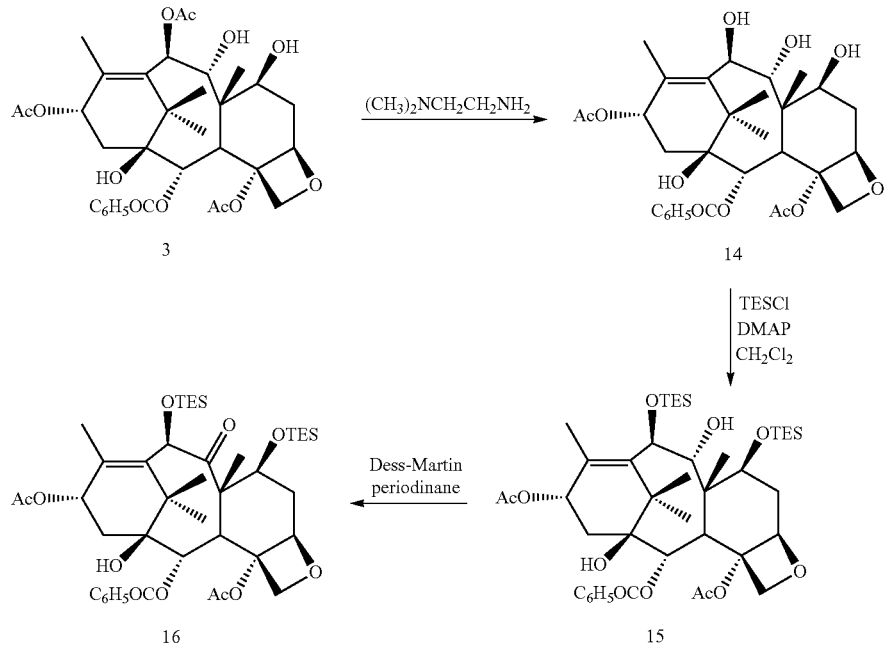

The present invention will be more readily understood by referring to the following examples which are given to illustrate the invention rather than to limit its scope.

EXAMPLE I

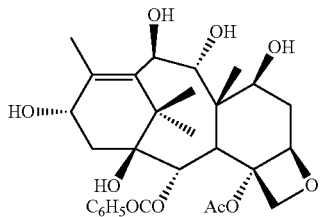

9-Dihydro-10-deacetylbaccatin III

9-Dihydro-13-acetylbaccatin III (200.0 g, 317 mmol) was added to 666 mL of hydrazine monohydrate. The heterogeneous mixture was stirred for 48 hours at room temperature. The mixture was filtered on sintered glass funnel and washed with cold water (2×333 mL) and the solid was dried under vacuum for 48 hours affording 168 g (97%) of 9-dihydro-10-deacetylbaccatin III. $^1$H NMR (Acetone-$d_6$, 600 MHz) δ 8.11 (dd; 2H; J=8.4, 1.2 Hz; o-Bz); 7.63 (br t; 2H; J=7.7 Hz; m-Bz); 7.52 (br t; 1H; J=7.5 Hz; p-Bz); 5.75 (d; 1H; J=5.9 Hz; H2); 5.61 (br s; 1H; 9-OH); 5.53 (br d; 1H; J=6.6 Hz; 7-OH); 4.88 (d; 1H; J=9.6 Hz; H5); 4.88 (d; 1H; J=9.6 Hz; H10); 4.84 (br t; 1H; J=8.1 Hz; H13); 4.41 (br m; 1H; J=9.6 Hz; H7); 4.30 (d; 1H; J=9.6 Hz; H9); 4.25 (d; 1H; J=5.1 Hz; 13-OH); 4.14 (d; 1H; J=7.9 Hz; H20a); 4.11 (d; 1H; J=7.9 Hz; H20b); 3.91 (br s; 1H; 10-OH); 3.31 (s; 1H; 1-OH); 3.18 (d; 1H; J=5.9 Hz; H3); 2.40 (o m; 1H; H6a); 2.40 (o m; 1H; H14a); 2.29 (dd; 1H; J=15.3, 9.6 Hz; H14b); 2.17 (s; 3H; Ac); 1.94 (d; 3H; J=1.1 Hz; Me-18); 1.81 (ddd; 1H; J=14.3, 10.1, 1.5 Hz; H6b); 1.77 (s; 3H; Me-19); 1.63 (s; 3H; Me-17); 1.15 (s; 3H; Me-16).

EXAMPLE II

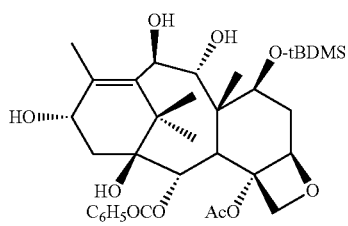

9-Dihydro-10-deacetyl-7-t-butyldimethylsilyl-baccatin III

To a stirred solution of 9-dihydro-10-deacetylbaccatin III (1.10 g, 2.01 mmol), triethylamine (2.02 g, 20.0 mmol) and DMAP (122 mg, 1.0 mmol) in 15 mL of dry dichloromethane was added t-butyldimethylsilylchloride (1.67 g, 5.5 mmol) and the reaction mixture was stirred for 24 hours at room temperature. The resulting mixture was quenched with water (100 mL) and extracted with ethyl acetate (1×100 mL and 2×50 mL). The combined organic extracts were washed with water (3×50 mL), dried over anhydrous $Na_2SO_4$ and concentrated to give a residue which was crystallized in 5:1 hexanes—acetone to afford 840 mg (63%) of 9-dihydro-10-deacetyl 7 t butyldimethylsilyl-baccatin III. $^1$H NMR (Acetone-$d_6$, 600 MHz) δ 8.11 (dd; 2H; J=8.2, 1.2 Hz; o-Bz); 7.63 (tt; 1H; J=7.4, 1.2 Hz; p-Bz); 7.52 (t; 2H; J=7.7 Hz; m-Bz); 5.73 (d; 1H; J=6.0 Hz; H2); 5.21 (d; 1H; J=9.6 Hz; 9-OH); 4.85 (br m; 1H; H13); 4.90 (d; 1H; J=9.3 Hz; H5); 4.81 (d; 1H; J=10.6 Hz; H10); 4.60 (dd; 1H; J=10.4, 7.0 Hz; H7); 4.34 (d; 1H; J=5.1 Hz; 13-OH); 4.21 (t; 1H; J=10.1 Hz; H9); 4.15 (d; 1H; J=7.9 Hz; H20a); 4.11 (d; 1H; J=7.9 Hz; H20b); 3.49 (s; 1H; 10-OH); 3.34 (s; 1H; 1-OH); 3.20 (d; 1H; J=6.0 Hz; H3); 2.45 (o m; 1H; H6a); 2.42 (o m; 1H; H14a);

2.31 (dd; 1H; J=14.9, 10.2 Hz; H14b); 2.18 (s; 3H; Ac); 1.98 (d; 3H; J=1.1 Hz; Me-18); 1.86 (ddd; 1H; J=14.1, 10.5, 1.6 Hz; H6b); 1.79 (s; 3H; Me-19); 1.63 (s; 3H; Me-17); 1.15 (s; 3H; Me-16); 0.96 (s; 9H; tBu); 0.29 (s; 3H; SiMe); 0.23 (s; 3H; SiMe).

EXAMPLE III

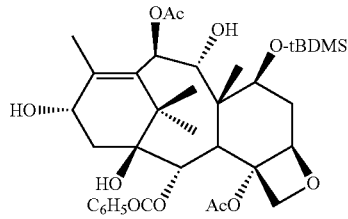

9-Dihydro-7-t-butyldimethylsilyl-baccatin III

Pyridine (50.0 mL) was cooled to 4° C. under argon and acetylchloride (4.04 g, 51.5 mmol) was added dropwise. The mixture was stirred for 10 min and a cold solution of 9-dihydro-10-deacetyl-7-t-butyldimethylsilyl-baccatin III (2.27 g, 3.43 mmol) in 10 mL of pyridine was added dropwise over 3 min. The reaction mixture was stirred for 6 hours at 4° C. under argon, quenched with water (50 mL) and extracted with ethyl acetate (1×500 mL and 2×100 mL). The combined organic extracts were washed with cold 1% HCl (3×25 mL), saturated aqueous sodium bicarbonate (1×50 mL) and water (3×100 mL). The resulting solution was dried over anhydrous $Na_2SO_4$ and evaporated. The product was isolated by flash chromatography ($SiO_2$; 2 to 20% acetone gradient in hexanes) affording 1.30 g (54%) of 9-dihydro-7-t-butyldimethylsilyl-baccatin III. $^1$H NMR (Acetone-$d_6$, 600 MHz) δ 8.12 (dd; 2H; J=8.1, 1.1 Hz; o-Bz); 7.63 (tt; 1H; J=7.4, 1.2 Hz; p-Bz); 7.53 (t; 2H; J=7.7 Hz; m-Bz); 6.05 (d; 1H; J=11.1 Hz; H10); 5.73 (d; 1H; J=6.6 Hz; H2); 5.00 (d; 1H; J=9.8 Hz; 9-OH); 4.91 (d; 1H; J=9.4 Hz; H5); 4.84 (br m; 1H; H13); 4.65 (dd; 1H; J=10.2, 7.2 Hz; H7); 4.38 (d; 1H; J=5.1 Hz; 13-OH); 4.36 (o t; 1H; H9); 4.16 (d; 1H; J=7.9 Hz; H20a); 4.12 (d; 1H; J=7.7 Hz; H20b); 3.48 (s; 1H; 1-OH); 3.17 (d; 1H; J=6.1 Hz; H3); 2.49 (ddd; 1H; J=14.3, 9.4, 7.2 Hz; H6a); 2.43 (dd; 1H; J=15.1, 6.2 Hz; H14a); 2.32 (m; 1H; H14b); 2.18 (s; 3H; Ac); 2.12 (d; 3H; J=1.3 Hz; Me-18); 2.02 (s; 3H; Ac); 1.85 (o m; 1H; H6b); 1.81 (s; 3H; Me-19); 1.62 (s; 3H; Me-17); 1.11 (s; 3H; Me-16); 0.92 (s; 9H; tBu); 0.30 (s; 3H; SiMe); 0.22 (s; 3H; SiMe).

EXAMPLE IV

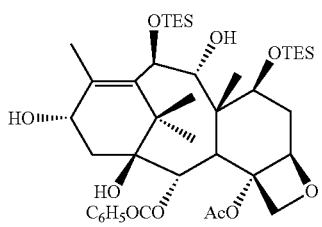

9-Dihydro-7,10-bis-triethylsilyl-10-deacetyl-baccatin III

To a stirred solution of 9-dihydro-10-deacetylbaccatin III (1.0 g, 1.83 mmol), triethylamine (1.85 g, 18.3 mmol) and DMAP (112 mg, 0.92 mmol) in 15 mL of dry dichloromethane was added triethylsilylchloride (1.21 g, 8.03 mmol) and the reaction mixture was stirred for 72 hours at room temperature. The resulting mixture was quenched with water (100 mL) and extracted with ethyl acetate (1×100 mL and 2×50 mL). The combined organic extracts were washed with water (3×50 mL), dried over anhydrous $Na_2SO_4$ and concentrated to give a residue which was crystallized in 5:1 hexanes—acetone to afford 714 mg (50.4%) of 9-dihydro-7,10-bis-triethylsilyl-10-deacetyl-baccatin III. $^1$H NMR (Acetone-$d_6$, 600 MHz) δ 8.10 (dd; 2H; J=8.2, 1.2 Hz; o-Bz); 7.63 (tt; 1H; J=7.4, 1.2 Hz; p-Bz); 7.52 (t; 2H; J=7.8 Hz; m-Bz); 5.75 (d; 1H; J=6.0 Hz; H2); 5.04 (d; 1H; J=9.6 Hz; 9-OH); 4.89 (d; 1H; J=9.3 Hz; H5); 4.84 (o m; 1H; H13); 4.84 (o d; 1H; J=10.0 Hz; H10); 4.62 (dd; 1H; J=10.2, 7.0 Hz; H7); 4.31 (d; 1H; J=5.1 Hz; 13-OH); 4.15 (o m; 1H; H9); 4.15 (o m; 1H; H20a); 4.11 (d; 1H; J=7.9 Hz; H20b); 3.30 (s; 1H; 1-OH); 3.19 (d; 1H; J=6.0 Hz; H3); 2.54 (ddd; 1H; J=14.0, 9.4, 7.2 Hz; H6a); 2.41 (ddd; 1H; J=15.3, 6.4, 2.0 Hz; H14a); 2.29 (dd; 1H; J=15.1, 10.0; H14b); 2.18 (s; 3H; Ac); 1.97 (d; 3H; J=1.1 Hz; Me-18); 1.88 (ddd; 1H; J=14.1, 10.3, 1.5 Hz; H6b); 1.79 (s; 3H; Me-19); 1.67 (s; 3H; Me-17); 1.16 (s; 3H; Me-16); 1.06 (t; 3H; J=7.9 Hz; $SiCH_2CH_3$); 1.00 (t; 3H; J=7.9 Hz; $SiCH_2CH_3$); 0.79 (q; 2H; J=7.7; $SiCH_2CH_3$); 0.69 (AB-q; 2H; $SiCH_2CH_3$).

EXAMPLE V

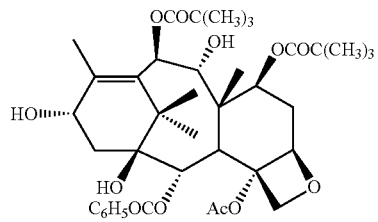

9-Dihydro-7,10-bis-tert-butyloxycarbonyl-10-deacetyl-baccatin III

To a stirred solution of 9-dihydro-10-deacetylbaccatin III (100 mg, 0.18 mmol) and DMAP (11 mg, 0.09 mmol) in 3 mL of dry dichloromethane was added di-tert-butyldicarbonate (94 mg, 0.43 mmol) and the reaction mixture was stirred for 48 hours at room temperature. The resulting mixture was quenched with water (50 mL) and extracted with ethyl acetate (3×50 mL). The combined organic extracts were washed with water (3×50 mL), dried over anhydrous $Na_2SO_4$ and evaporated. The product was isolated by flash chromatography ($SiO_2$; 0 to 25% acetone gradient in hexanes) affording 65 mg (48%) of 9-dihydro-7,10-bis-tert-butyloxycarbonyl-10-deacetyl-baccatin III. $^1$H NMR (Acetone-$d_6$, 600 MHz) δ 8.11 (dd; 2H; J=8.1, 1.1 Hz; o-Bz); 7.64 (tt; 1H; J=7.4, 1.2 Hz; p-Bz); 7.53 (t; 2H; J=7.8 Hz; m-Bz); 6.02 (d; 1H; J=11.1 Hz; H10); 5.75 (d; 1H; J=5.9 Hz; H2); 5.38 (dd; 1H; J=10.1, 7.5 Hz; H7); 4.95 (d; 1H; J=8.9 Hz; H5); 4.88 (br t; 1H; J=8.3; H13); 4.41 (d; 1H; J=5.1 Hz; 13-OH); 4.37 (m; 1H; H9); 4.17 (d; 1H; J=7.9; H20a); 4.11 (d; 1H; J=7.7 Hz; H20b); 3.59 (s; 1H; 1-OH); 3.54 (d; 1H; J=9.4 Hz; 9-OH); 3.21 (d; 1H; J=6.0 Hz; H3); 2.55 (ddd; 1H; J=14.5, 8.9, 7.7 Hz; H6a); 2.43 (ddd; 1H; J=15.3, 6.3, 1.9 Hz; H14a); 2.34 (dd; 1H; J=15.8, 10.5;

H14b); 2.20 (s; 3H; Ac); 2.12 (br s; 3H; Me-18); 1.80 (ddd; 1H; J=14.4, 10.2, 1.3 Hz; H6b); 1.83 (s; 3H; Me-19); 1.58 (s; 3H; Me-17); 1.50 (s; 9H, tBu); 1.46 (s; 9H, tBu); 1.13 (s; 3H; Me-16).

EXAMPLE VI

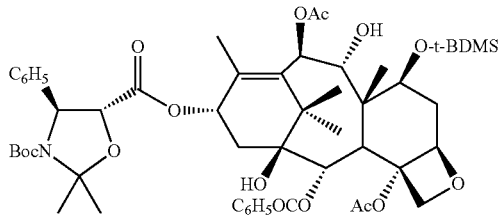

13-[(2R,3S)—N-t-Butyloxycarbonyl-N,O-(1-methylethylidene)-3-phenylisoserine]-9-dihydro-7-t-butyldimethylsilyl-baccatin III To a stirred solution of 9-dihydro-7-t-butyldimethylsilyl-baccatin III (225 mg, 0.32 mmol), (4S,5R)-3-tert-butyloxyxcarbonyl-2,2-dimethyl-4-phenyl-5-oxazolidinecarboxylic acid (154 mg, 0.50 mmol) and DMAP (20 mg, 0.16 mmol) in 3 mL of dry toluene was added N,N,-dicyclohexylcarbodiimide (105 mg, 0.51 mmol). The solution was stirred for 45 minutes under argon at room temperature and filtered. Water (50 mL) was added and the solution was extracted with ethyl acetate (3×50 mL). The combined organic extracts were washed with water (3×50 mL), sodium bicarbonate (1×50 mL) and water (3×50 mL). The solution was dried over anhydrous $Na_2SO_4$ and evaporated to dryness affording 320 mg (99%) of compound 8. $^1$H NMR (Acetone-d6, 600 MHz) δ 8.06 (d; 2H; J=7.7 Hz; o-Bz); 7.65 (t; 1H; J=7.5 Hz; p-Bz); 7.54 (t; 2H; J=7.7 Hz; m-Bz); 7.43-7.40 (m; 5H; 3'-Ph); 6.27 (br t; 1H; J=8.8 Hz; H13); 6.04 (d; 1H; J=11.0 Hz; H10); 5.78 (d; 1H; J=6.0 Hz; H2); 5.14 (br s; 1H; H3'); 5.04 (d; 1H; J=9.8 Hz; 9-OH); 4.84 (d; 1H; J=9.1 Hz; H5); 4.65 (o d; 1H; J=6.2 Hz; H2'); 4.60 (dd; 1H; J=9.8, 7.6 Hz; H7); 4.40 (t; 1H; J=10.5 Hz; H9); 4.11 (s; 2H; H20ab); 3.90 (s; 1H, 1-OH); 3.07 (d; 1H; J=6.0 Hz; H3); 2.48 (ddd; 1H; J=14.3, 9.1, 7.6 Hz; H6a); 2.39 (dd; 1H; J=15.1, 9.8 Hz; H14a); 2.32 (o m; 1H; H14b); 2.04 (s; 3H; Ac); 2.04 (s; 3H; Me-18); 1.85 (o m; 1H; H6b); 1.81 (s; 3H; Ac); 1.81 (o s; 3H; Me-19); 1.79 (o s; 3H; NCMe$_2$); 1.69 (s; 3H; Me-17); 1.72 (s; 3H; NCMe$_2$); 1.26 (s; 3H; Me-16); 1.11 (br s; 9H, BOC tBu); 0.92 (s; 9H; TBDMS tBu); 0.29 (s; 3H; SiMe); 0.22 (s; 3H; SiMe).

EXAMPLE VII

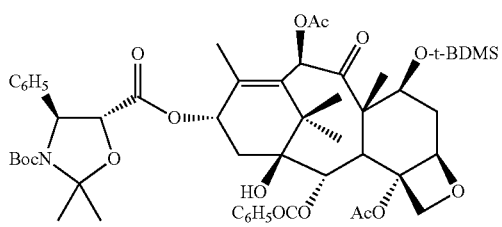

13-[(2R,3S)—N-t-Butyloxycarbonyl-N,O-(1-methylethylidene)-3-phenylisoserine]-7-t-butyldimethylsilyl-baccatin III To a stirred mixture of Dess-Martin periodinane (227 mg, 268 mmol) in 5.0 mL of dichloromethane was added pyridine (0.3 mL) until the mixture became clear. Compound 8 (300 mg, 0.28 mmol) was dissolved in 2.0 mL of dichloromethane and added to the periodinane solution. The reaction mixture was gently stirred for 5 hours at room temperature and cold saturated sodium hydrogensulfite (50 mL) was added. The mixture was extracted with ethyl acetate (3×50 mL) and the combined organic extracts were washed with water (3×50 mL), dried over anhydrous $Na_2SO_4$ and evaporated to dryness. The product was isolated by flash chromatography ($SiO_2$; 2 to 12% acetone gradient in hexanes) affording 276 mg (92%) of compound 9. $^1$H NMR (Acetone-d$_6$, 600 MHz) δ $^1$H NMR (Acetone-d$_6$, 600 MHz) δ 8.06 (dd; 2H; J=8.1, 1.1 Hz; o-Bz); 7.67 (t; 1H; J=7.5 Hz; p-Bz); 7.56 (t; 2H; J=7.7 Hz; m-Bz); 7.49-7.43 (m; 5H; 3'-Ph); 6.27 (br t; 1H; J=8.8 Hz; H13); 6.40 (s; 1H; H10); 5.70 (d; 1H; J=6.8 Hz; H2); 5.11 (br s; 1H; H3'); 4.87 (d; 1H; J=9.1 Hz; H5); 4.64 (d; 1H; J=6.4 Hz; H2'); 4.45 (dd; 1H; J=10.2, 7.0 Hz; H7); 4.10 (d AB; 2H; J=8.5 Hz; H20ab); 3.83 (d; 1H; J=7.2 Hz; H3); 2.51 (ddd; 1H; J=14.3, 9.4, 7.0 Hz; H6a); 2.42 (dd; 1H; J=15.8, 9.0 Hz; H14a); 2.34 (dd; 1H; J=15.0, 9.2 Hz; H14b); 2.12 (d; 3H; J=0.9 Hz; Me-18); 2.10 (s; 3H; Ac); 1.90 (s; 3H; Ac); 1.80 (s; 3H; NCMe$_2$); 1.73 (o m; 1H; H6b); 1.73 (s; 3H; NCMe$_2$); 1.68 (s; 3H; Me-19); 1.25 (s; 3H; Me-17); 1.21 (s; 3H; Me-16); 1.10 (br s; 9H, BOC tBu); 0.79 (s; 9H; TBDMS tBu); 0.12 (s; 3H; SiMe); 0.08 (s; 3H; SiMe).

EXAMPLE VIII

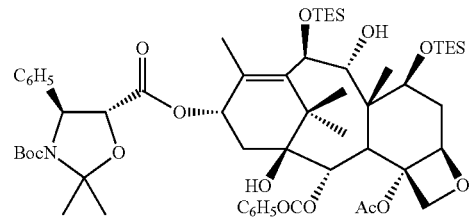

13-[(2R,3S)—N-t-Butyloxycarbonyl-N,O-(1-methylethylidene)-3-phenylisoserine]-9-dihydro-7,10-bis-triethylsilyl-10-deacetyl-baccatin III To a stirred solution of 9-dihydro-7,10-bis-triethylsilyl-10-deacetyl-baccatin III (714 mg, 0.92 mmol), (4S,5R)-3-tert-butyloxyxcarbonyl-2,2-dimethyl-4-phenyl-5-oxazolidinecarboxylic acid (451 mg, 1.46 mmol) and DMAP (57 mg, 0.47 mmol) in 10 mL of dry toluene was added N,N,-dicyclohexylcarbodiimide (308 mg, 1.49 mmol). The solution was stirred for 30 minutes under argon at room temperature and filtered. Water (50 mL) was added and the solution was extracted with ethyl acetate (3×50 mL). The combined organic extracts were washed with water (3×50 mL), sodium bicarbonate (1×50 mL) and water (3×50 mL). The solution was dried over anhydrous $Na_2SO_4$ and evaporated to dryness affording 957 mg (96%) of compound 11. $^1$H NMR (Acetone-d$_6$, 600 MHz) δ 8.05 (d; 2H; J=7.4 Hz; o-Bz); 7.64 (t; 1H; J=7.5 Hz; p-Bz); 7.52 (t; 2H; J=7.9 Hz; m-Bz); 7.42-7.32

(m; 5H; 3'-Ph); 6.26 (br t; 1H; J=8.8 Hz; H13); 5.77 (d; 1H; J=6.0 Hz; H2); 5.14 (br s; 1H; H3'); 5.06 (d; 1H; J=9.6 Hz; 9-OH); 4.84 (o d; 1H; J=9.8 Hz; H10); 4.82 (o d; 1H; J=8.5 Hz; H5); 4.61 (d; 1H; J=6.0 Hz; H2'); 4.57 (dd; 1H; J=9.4, 7.7 Hz; H7); 4.17 (o m; 1H; H9); 4.10 (s; 2H; H20ab); 3.08 (d; 1H; J=5.9 Hz; H3); 2.53 (m; 1H; H6a); 2.34 (m; 2H; H14ab); 1.88 (s; 3H; Me-18); 1.88 (o m; 1H; H6b); 1.79 (s; 3H; Ac); 1.79 (o s; 3H; Me-19); 1.79 (o s; 3H; NCMe$_2$); 1.72 (s; 3H; Me-17); 1.71 (o s; 3H; NCMe$_2$); 1.33 (s; 3H; Me-16); 1.10 (br s; 9H, tBu); 1.05 (t; 3H; J=8.0 Hz; SiCH$_2$CH$_3$); 1.00 (t; 3H; J=7.9 Hz; SiCH$_2$CH$_3$); 0.79 (m; 2H; SiCH$_2$CH$_3$); 0.68 (m; 2H; SiCH$_2$CH$_3$).

EXAMPLE IX

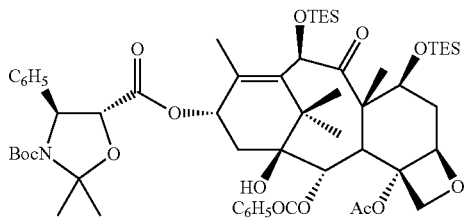

13-[(2R,3S)—N-t-Butyloxycarbonyl-N,O-(1-methyl-ethylidene)-3-phenylisoserine]-7,10-bis-triethylsilyl-10-deacetyl-baccatin III To a stirred mixture of Dess-Martin periodinane (1.11 g, 1.31 mmol) in 30.0 mL of dichloromethane was added pyridine (2.0 mL) until the mixture became clear. Compound 11 (1.40 g, 1.30 mmol) was dissolved in 10.0 mL of dichloromethane and added to the periodinane solution. The reaction mixture was gently stirred for 3 hours at room temperature and cold saturated sodium hydrogensulfite (50 mL) was added. The mixture was extracted with ethyl acetate (3×50 mL) and the combined organic extracts were washed with water (3×50 mL), dried over anhydrous Na$_2$SO$_4$ and evaporated to dryness affording 1.30 g (93%) of compound 12. $^1$H NMR (Acetone-d$_6$, 600 MHz) δ 8.05 (d; 2H; J=8.3 Hz; o-Bz); 7.55 (t; 2H; J=7.7 Hz; m-Bz); 7.46 (t; 1H; J=7.5 Hz; p-Bz); 7.43 (m; 5H; 3'-Ph); 6.27 (t; 1H; J=8.6 Hz; H13); 5.67 (o d; 1H; J=7.2 Hz; H2); 5.24 (s; 1H; H10); 5.10 (br s; 1H; H3'); 4.86 (d; 1H; J=8.9 Hz; H5); 4.63 (d; 1H; J=6.6 Hz; H2'); 4.46 (dd; 1H; J=10.4, 6.8 Hz; H7); 4.11 (d; 1H; J=8.3 Hz; H20a); 4.08 (d; 1H; J=8.1 Hz; H20b); 3.85 (d; 1H; J=7.2 Hz; H3); 2.55 (ddd; 1H; J=14.1, 9.4, 6.9 Hz; H6a); 2.38 (dd; 1H; J=15.1, 9.1 Hz H14a); 2.33 (dd; 1H; J=15.2, 9.2 Hz H14b); 1.96 (s; 3H; Me-18); 1.86 (br s; 3H; Ac); 1.80 (o m; 1H; H6b); 1.80 (s; 3H; NCMe$_2$); 1.72 (s; 3H; NCMe$_2$); 1.64 (s; 3H; Me-19); 1.25 (s; 3H; Me-17); 1.25 (s; 3H; Me-16); 1.1 (br s; 9H, tBu); 1.03 (t; 3H; J=7.9 Hz; SiCH$_2$CH$_3$); 0.99 (t; 3H; J=8.0 Hz; SiCH$_2$CH$_3$); 0.69 (m; 2H; SiCH$_2$CH$_3$); 0.63 (q; 2H; J=7.9 Hz; SiCH$_2$CH$_3$).

EXAMPLE X

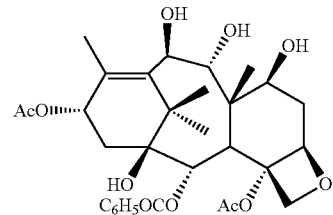

9-dihydro-10-deacetyl-13-acetylbaccatin III

A solution of 9-dihydro-13-acetylbaccatin III (500 mg, 0.79 mmol) in 4.0 mL of N,N-dimethylethylenediamine was stirred for 48 hours at room temperature. The solution was evaporated and the residue was taken up in 1.5 mL of toluene and evaporated to dryness. The solid was separated by chromatography (Alumina; 2 to 20% methanol gradient in chloroform) affording 397 mg (85%) of 9-dihydro-10-deacetyl-13-acetylbaccatin III. $^1$H NMR (Acetone-d$_6$, 600 MHz) δ 8.10 (dd; 2H; J=8.1, 1.1 Hz; o-Bz); 7.63 (t; 1H; J=7.5 Hz; p-Bz); 7.52 (t; 2H; J=7.7 Hz; m-Bz); 6.16 (br t; 1H; J=8.5 Hz; H13); 5.80 (d; 1H; J=6.0 Hz; H2); 4.90 (d; 1H; J=10.2 Hz; H5); 4.90 (d; 1H; J=10.2 Hz; H10); 4.37 (dd; 1H; J=9.8, 7.7 Hz; H7); 4.33 (d; 1H; J=10.4 Hz; H9); 4.15 (d; 1H; J=7.9 Hz; H20a); 4.13 (d; 1H; J=7.7 Hz; H20b); 3.67 (s; 1H; 1-OH); 3.10 (d; 1H; J=5.9 Hz; H3); 2.43 (ddd; 1H; J=14.8, 9.2, 7.7 Hz; H6a); 2.38 (dd; 1H; J=15.1, 7.7 Hz; H14a); 2.25 (dd; 1H; J=15.0, 9.3 Hz; H14b); 2.29 (s; 3H; Ac); 2.16 (s; 3H; Ac); 1.81 (d; 3H; J=1.3 Hz; Me-18); 1.82 (o m; 1H; H6b); 1.78 (s; 3H; Me-19); 1.69 (s; 3H; Me-17); 1.27 (s; 3H; Me-16).

EXAMPLE XI

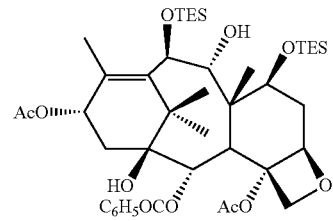

9-Dihydro-7,10-bis-triethylsilyl-10-deacetyl-13-acetyl-baccatin III

To a stirred solution of 9-dihydro-10-deacetyl-13-acetyl-baccatin III (1.0 g, 1.70 mmol), triethylamine (1.72 g, 17.0 mmol) and DMAP (104 mg, 0.85 mmol) in 15 mL of dry dichloromethane was added triethylsilylchloride (1.13 g, 7.5 mmol) and the reaction mixture was stirred for 72 hours at room temperature. The resulting mixture was quenched with water (100 mL) and extracted with ethyl acetate (1×100 mL and 2×50 mL). The combined organic extracts were washed with water (3×50 mL), dried over anhydrous Na$_2$SO$_4$ and concentrated to give a residue which was crystallized in 5:1 hexanes—acetone to afford 626 mg (45%) of 9-dihydro-7,10-bis-triethylsilyl-10-deacetyl-13-acetyl-baccatin III. NMR (Acetone-d$_6$, 600 MHz) δ 8.10 (dd; 2H; J=8.3, 1.1 Hz; o-Bz);

7.63 (tt; 1H; J=7.4, 1.2 Hz; p-Bz); 7.52 (t; 2H; J=7.7 Hz; m-Bz); 6.14 (tq; 1H; J=9.0, 1.0 Hz; H13); 5.79 (d; 1H; J=6.0 Hz; H2); 5.05 (d; 1H; J=9.6 Hz; 9-OH); 4.91 (d; 1H; J=9.3 Hz; H5); 4.84 (d; 1H; J=10.0 Hz; H10); 4.57 (dd; 1H; J=9.7, 7.5 Hz; H7); 4.12 (o m; 1H; H9); 4.15 (o m; 2H; H20ab); 3.75 (s; 1H; 1-OH); 3.12 (d; 1H; J=6.0 Hz; H3); 2.57 (ddd; 1H; J=14.2, 9.2, 7.4 Hz; H6a); 2.37 (dd; 1H; J=15.1, 7.9 Hz; H14a); 2.28 (dd; 1H; J=15.2, 10.4; H14b); 2.30 (s; 3H; Ac); 2.17 (s; 3H; Ac); 1.90 (ddd; 1H; J=14.1, 10.3, 1.3 Hz; H6b); 1.84 (d; 3H; J=1.3 Hz; Me-18); 1.81 (s; 3H; Me-19); 1.71 (s; 3H; Me-17); 1.28 (s; 3H; Me-16); 1.06 (t; 3H; J=8.0 Hz; SiCH$_2$CH$_3$); 1.00 (t; 3H; J=7.9 Hz; SiCH$_2$CH$_3$); 0.79 (q; 2H; J=8.2; SiCH$_2$CH$_3$); 0.69 (m; 2H; SiCH$_2$CH$_3$).

EXAMPLE XII

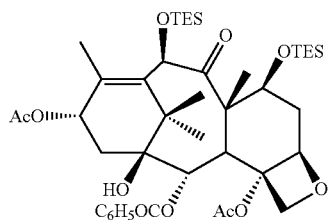

7,10-bis-Triethylsilyl-10-deacetyl-13-acetyl-baccatin III

To a stirred mixture of Dess-Martin periodinane (66 mg, 0.16 mmol) in 2.0 mL of dichloromethane was added pyridine (0.1 mL) until the mixture became clear. 9-dihydro-7,10-bis-triethylsilyl-10-deacetyl-13-acetyl-baccatin III (100 mg, 0.12 mmol) was dissolved in 1.0 mL of dichloromethane and added to the periodinane solution. The reaction mixture was gently stirred for 18 hours at room temperature and cold saturated sodium hydrogensulfite (2 mL) was added. The mixture was extracted with ethyl acetate (1×50 mL and 2×25 mL) and the combined organic extracts were washed with water (3×25 mL), dried over anhydrous Na$_2$SO$_4$ and evaporated to dryness. The product was isolated by flash chromatography (SiO$_2$; 2 to 10% acetone gradient in hexanes) affording 82 mg (82%) of 7,10-bis-Triethylsilyl-10-deacetyl-13-acetyl-baccatin III. $^1$H NMR (Acetone-d$_6$, 600 MHz) δ 8.08 (dd; 2H; J=8.2, 1.0 Hz; o-Bz); 7.63 (t; 1H; J=7.5 Hz; p-Bz); 7.52 (t; 2H; J=7.7 Hz; m-Bz); 6.13 (t; 1H; J=8.4 Hz; H13); 5.69 (d; 1H; J=7.0 Hz; H2); 5.26 (s; 1H; H10); 4.94 (d; 1H; J=8.9 Hz; H5); 4.49 (dd; 1H; J=10.6, 6.8 Hz; H7); 4.15 (s; 2H; H20ab); 3.91 (d; 1H; J=7.0 Hz; H3); 3.69 (s; 1H; 1-OH); 2.59 (ddd; 1H; J=14.1, 9.5, 6.8 Hz; H6a); 2.41 (ddd; 1H; J=15.3, 8.6, 1.3 Hz; H14a); 2.36 (s; 3H; Ac); 2.33 (dd; 1H; J=15.3, 9.4; H14b); 2.19 (s; 3H; Ac); 1.94 (d; 3H; J=1.3 Hz; Me-18); 1.82 (o m; 1H; H6b); 1.67 (s; 3H; Me-19); 1.24 (s; 3H; Me-17); 1.20 (s; 3H; Me-16); 1.03 (t; 3H; J=7.9 Hz; SiCH$_2$CH$_3$); 1.00 (t; 3H; J=7.7 Hz; SiCH$_2$CH$_3$); 0.70 (m; 2H; SiCH$_2$CH$_3$); 0.64 (q; 2H; J=8.0 Hz; SiCH$_2$CH$_3$).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:
1. A process for the preparation of compound of formula V

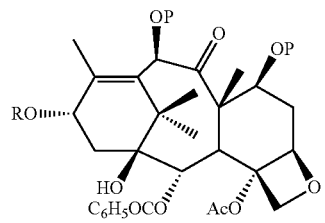

wherein P is a hydroxy protecting group and R is acetyl, said process comprising the steps of:
  i) selectively deacetylating the 10-hydroxy group of 9-dihydro-13-acetylbaccatin III having the formula:

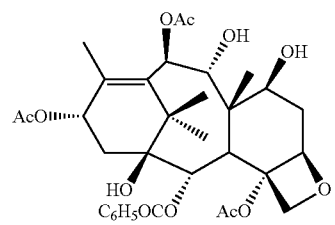

with N,N-dimethylethylenediamine to produce 9-dihydro-10-deacetyl-13-acetyl-baccatin III of formula:

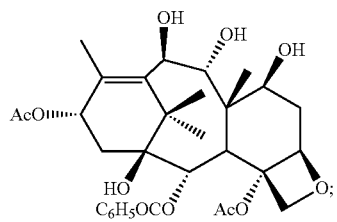

ii) concomitantly protecting 7-hydroxy and 10-hydroxy groups of the reaction product of step i); and
  iii) oxidizing the 9-hydroxy group of the reaction product of step ii) with an oxidizing agent to produce the compound of formula V.

2. The process of claim 1, wherein the oxidizing agent is selected from the group consisting of o-iodoxybenzoic acid (IBX), 1,1,1-triacetoxy-1,1-dihydro-1,2-benziodoxol-3 (1H)-one (Dess-Martin periodinane), iodosobenzene, iodozobenzene diacetate, CrO$_3$/H$_2$SO$_4$ (Jone's reagent), pyridinium dichromate, pyridinium chlorochromate, potassium permanganate and Swern reagent.

3. The process of claim 1, wherein the oxidizing agent is 1,1,1-triacetoxy-1,1-dihydro-1,2-benziodoxol-3(1H)-one (Dess-Martin periodinane).

* * * * *